(12) United States Patent
Abdennour et al.

(10) Patent No.: US 7,331,787 B2
(45) Date of Patent: *Feb. 19, 2008

(54) CHARACTERIZATION OF AN ANTIBIOTIC IMPREGNATED DELIVERY SYSTEM AS AN INTRACANAL MEDICAMENT IN ENDODONTIC THERAPY

(75) Inventors: Mario Abdennour, Newton, MA (US); Philip Stashenko, Medfield, MA (US); Michele Scrime, Manalapan, NJ (US); Jack Gilad, Chestnut Hill, MA (US); Max Goodson, Cambridge, MA (US)

(73) Assignee: Novalar Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/812,638

(22) Filed: Mar. 29, 2004

(65) Prior Publication Data

US 2004/0191722 A1 Sep. 30, 2004

Related U.S. Application Data

(63) Continuation of application No. 09/963,880, filed on Sep. 26, 2001, now Pat. No. 6,712,610, and a continuation-in-part of application No. 09/540,088, filed on Mar. 31, 2000, now abandoned.

(60) Provisional application No. 60/240,004, filed on Oct. 12, 2000, provisional application No. 60/127,497, filed on Apr. 2, 1999.

(30) Foreign Application Priority Data

Mar. 30, 2001 (CA) ..................... 2343471

(51) Int. Cl.
*A61C 5/02* (2006.01)

(52) U.S. Cl. ....................................... 433/81

(58) Field of Classification Search .................. 433/80, 433/81, 102, 224
See application file for complete search history.

(56) References Cited

U.S. PATENT DOCUMENTS 4,003,810 A * 1/1977 Hoyt et al. ................... 525/60

(Continued)

FOREIGN PATENT DOCUMENTS

EP 0 140 766 A2 5/1985

(Continued)

OTHER PUBLICATIONS

Grossman, L.I., "Polyantibiotic Treatment of Pulpless Teeth," *The Journal of the American Dental Association*, 43(3):265-278 (1951).

(Continued)

*Primary Examiner*—Melba Bumgarner
(74) *Attorney, Agent, or Firm*—Sterne, Kessler, Goldstein & Fox P.L.L.C.

(57) ABSTRACT

Endodontic fibers comprising a biocompatible polymer vehicle permeable to medicaments, or combinations of medicaments are described. Such fibers can be used, for example, in a method for the local delivery and sustained release of medicaments to periodontal or intracanal treatment sites. Endodontic fibers described include modified periodontal fibers and intracanal fibers.

34 Claims, 10 Drawing Sheets

COMPARISON OF ANTIBACTERIAL ACTIVITY
OF CLINDAMYCIN FIBER vs Ca(OH)$_2$-GUTTA-PERCHA
IN EXTRACTED HUMAN TEETH

U.S. PATENT DOCUMENTS

| | | | | |
|---|---|---|---|---|
| 4,175,326 | A | * | 11/1979 | Goodson ..................... 433/80 |
| 4,666,897 | A | * | 5/1987 | Golub et al. ................ 514/152 |
| 4,764,377 | A | | 8/1988 | Goodson |
| 4,892,736 | A | | 1/1990 | Goodson |
| 5,114,718 | A | | 5/1992 | Damani |

FOREIGN PATENT DOCUMENTS

| | | |
|---|---|---|
| JP | S63-303922 | 12/1988 |

OTHER PUBLICATIONS

Sjögren, U. et al., "Influence of Infection at the Time of Root Filling on the Outcome of Endodontic Treatment of Teeth with Apical Periodontitis," *International Endodontic Journal*, 30:297-306 (1997).

Haapasalo, M., "Black-Pigmented Gram-Negative Anaerobes in Endodontic Infections," *FEMS Immunology and Medical Microbiology*, 6(2&3):213-218 (1993).

Nagaoka, S., et al., "Bacterial Invasion into Dentinal Tubules of Human Vital and Nonvital Teeth," *Journal of Endodontics*, 21(2):70-73 (1995).

Yoshida, M., et al., "Correlation between Clinical Symptoms and Microorganisms Isolated from Root Canals of Teeth with Periapical Pathosis," *Journal of Endodontics*, 13(1):24-28 (1987).

Woods, R., "Twenty Years of Antibiotic Sensitivity Testing of Dental Infections. Part 2. A Review, 1966-1986," *Australian Dental Journal*, 33(6):505-510 (1988).

Byström, A., et al., "Bacteriologic Evaluation of the Effect of 0.5 Percent Sodium Hypochlorite in Endodontic Therapy," *Oral. Surg. Oral. Med Pathol.*, 55(3):307-312 (1983).

Goodson, J.M., et al., "Monolithic Tetracycline-containing Fibers for Controlled Delivery to Periodontal Pockets," *Journal of Periodontology*, 54(10):575-579 (1983).

Gilad, J.Z., "Development of a Clindamycin Impregnanted EVA Fiber as an Intracanal Medicament in Endodontic Therapy," Master's Thesis, Harvard University School of Dental Medicine, (Apr. 1998).

Chong, B.S. and T.R. Pitt Ford, "The Role of Intracanal Medication in Root Canal Treatment," *International Endodontic Journal*, 25:97-106 (1992).

Tanriverdi, F., et al., "An In Vitro Test Model for Investigation of Disinfection of Dentinal Tubules Infected with *Enterococcus faecalis*," *Braz. Dent. J.*, 8(2):67-72 (1997).

Rimmer, A., "Intracanal Medications and Antibiotics in the Control of Interappointment Flare-ups," *Quintessence Int.*, 22(12):997-1005 (1991).

Walton, R. and A. Fouad, "Endodontic Interappointment Flare-ups: A Prospective Study of Incidence and Related Factors," *J. Endod.*, 18(4):172-177 (1992).

Seymour, R.A. and P.A. Heasman, "Pharmacological Control of Periodontal Disease. II. Antimicrobial Agents," *J. Dent.*, 23(1):5-14 (1995).

Barbosa, C.A.M., et al., "Evaluation of the Antibacterial Activities of Calcium Hydroxide, Chlorhexidine, and Camphorated Paramonochorophenol as Intracanal Medicament. A Clinical and Laboratory Study," *J. Endod.*, 23(1):297-300 (1997).

Tanner, A. and N. Stillman, "Oral and Dental Infections with Anaerobic Bacteria: Clinical Features, Predominant Pathogens and Treatment," *Clin. Infect. Dis.*, 16(Supp. 4):S304-S309 (1993).

Morse, D.R., et al., "Infectious Flare-ups and Serious Sequelae Following Endodontic Treatment: A Prospective Randomized Trial on Efficacy of Antibiotic Prophylaxis in Cases of Asymtomatic Pulpal-Periapical Lesions," *Oral Surg. Oral Med. Oral Pathol.*, 64:96-109 (1987).

Gomes, B.P., et al., "Clinical Significance of Dental Root Canal Microflora," *J. Dent.*, 24(1-2):47-55 (1996).

Cheung, G.S.P., "Endodontic Failures—Changing the Approach," *Int. Dent. J.*, 46:131-138 (1996).

Gomes, B.P., F.A., et al., "Variations in the Susceptibilities of Components of the Endodontic Microflora to Biomechanical Procedures," *Int. Endod. J.*, 29:235-241 (1996).

Love, R.M., "Clinical Management of Infected Root Canal Dentin," *Pract. Periodontics Aesthet. Dent.*, 8(6):581-584 (1996).

Hayashi, K., et al., "Clinical and Microbiological Effects of Controlled-release Local Delivery of Minocycline on Periodontitis in Dogs," *Am. J. Vet. Res.*, 59(4):464-467 (1998).

Killoy, W.J. and A.M. Polson, "Controlled Local Delivery of Antimicrobials in the Treatment of Periodontitis," *Advances in Periodontics, Part 1*, 42(2):263-283 (1998).

Mombelli, A., et al., "Topographic Distribution of Black-pigmented Anaerobes Before and After Periodontal Treatment by Local Delivery of Tetracycline," *J. Clin. Periodontol.*, 23:906-913 (1996).

Walker, C. and J. Gordon, "The Effect of Clindamycin on the Microbiota Associated with Refractory Periodontitis," *J. Periodontol.*, 61(11):692-698 (1990).

Goodson, J.M., et al., "Multicenter Evaluation of Tetracycline Fiber Therapy: I. Experimental Design, Methods, and Baseline Data," *J. Periodont. Res.*, 26:361-370 (1991).

Goodson, J.M., et al., "Multicenter Evaluation of Tetracycline Fiber Therapy: II. Clinical Response," *J. Periodont. Res.*, 26:371-379 (1991).

Greenstein, G. and A. Polson, "The Role of Local Drug Delivery in the Management of Periodontal Diseases: A Comprehensive Review," *J. Periodontol.*, 69:507-520 (1998).

Somayaji, B.V., et al., "Evaluation of Antimicrobial Efficacy and Release Pattern of Tetracycline and Metronidazole Using a Local Delivery System," *J. Periodontol.*, 69:409-413 (1998).

Abbott, P.V., "Medicaments: Aids to Success in Endodontics. Part 1. A Review of the Literature," *Aust. Dent. J.*, 35(5):438-448 (1990).

Gergely, J.M. and P.M. DiFiore, "Intracanal Medication in Endodontic Treatment: A Survey of Endodontic Programs," *General Dentistry*, Jul.-Aug.:328-331 (1993).

Matusow, R.J., "The Flare-up Phenomenon in Endodontics: A Clinical Perspective and Review," *Oral Surg. Oral Med. Oral Pathol.*, 65(6):750-753 (1988).

\* cited by examiner

NUMBER BACTERIAL CFUs (x10⁴)
COMPARISON OF MEANS - 4 TREATMENTS

|  | PRE TX | POST TX | CRUSHED |
|---|---|---|---|
| PLAIN | 496 | 549 | 676 |
| CLINDAMYCIN | 629 | 82 | 90 |
| ROEKO | 672 | 564 | 647 |
| CALCIUM HYDROXIDE | 577 | 42 | 38 |

CHARACTERIZATION OF AN ANTIBIOTIC IMPREGNATED DELIVERY SYSTEM AS AN INTRACANAL MEDICAMENT IN ENDODONTIC THERAPY

RELATED APPLICATIONS

This application is a continuation of U.S. patent application Ser. No. 09/963,880, filed Sep. 26, 2001, now U.S. Pat. No. 6,712,610 which claims the benefit of U.S. Provisional Application No. 60/240,004, filed Oct. 12, 2000, and is a continuation-in-part of U.S. patent application Ser. No. 09/540,088, filed Mar. 31, 2000, now abandoned which claims the benefit of U.S. Provisional Application No. 60/127,497, filed Apr. 2, 1999. This application also claims priority to Canadian Patent Application No. 2343471, filed Mar. 30, 2001. The entire teachings of the above-referenced applications are incorporated herein by reference.

BACKGROUND OF THE INVENTION

Endodontics is a field of dentistry concerned with the biology and pathology of the dental pulp and periapical tissues. Endodontic treatment employs a set of techniques, such as chemomechanical debridement, irrigation, drainage of hard and soft tissue, trephination, and antimicrobial therapy, with the goal of avoiding the extraction of a damaged, infected or diseased tooth.

Normal vital pulp is sterile, and the role of bacterial infection in the pathogenesis of pulpal and periapical disease is well established. Infected or necrotic pulpal tissue renders the pulp chamber and root canal a potential reservoir of bacteria, and disinfection of the tooth is one of the primary justifications for the chemomechanical aspects of root canal therapy. Recent data demonstrate a high incidence of root canal failure in necrotic teeth treated in a single visit, attributed to bacteria remaining in complex anatomical spaces such as accessory canals, fins, deltas and isthmuses (Sjorgen et al., *Int. Endo. J.*, 30:297-306 (1997)). Other studies have reported the ability of bacteria to migrate into dentinal tubules and survive therein (Nagaoka et al., *J. Endodon.*, 21:70-73 (1995)). It is speculated that the success rate of endodontic treatment could be 26% higher if the root canal is successfully disinfected prior to the final restoration (Sjorgen et al., *Int. Endo. J.*, 30:297-306 (1997)).

Root canal infections are characterized as polymicrobial infections which tend to 10 be dominated by anaerobic bacteria. As a group, the common endodontic microbes associated with treatment failure include *F. nucleatum*, *P. intermedia*, *P. micros*, *S. intermedius*, *P. endodontlis*, *P. gingivalis*, *P. melaninogenica*, *E. lentum*, *V. parvula*, *S. sanguis*, *P. buccae*, *P. oralis*, and *P. acnes*. (Haapasalo, *FEMS Immunol. and Medical Micro.* 6:213-217 (1993) and Sundqvist, *J. Endodon.*, 7:257-262 (1992)).

Post-operative periapical pain and interappointment flare-ups are also routinely attributed to the presence of bacteria, and/or their by-products, within the root canal. Typically, an initial bacterial infection triggers a host-mediated inflammatory response, the consequences of which underlie the flare-up patient's clinical symptoms. It has been reported that bacteria surviving instrumentation and irrigation proliferate rapidly in empty root canals (Bystrom and Sundqvist, *Oral. Surg. Oral. Med. Oral Pathol.*, 55:307-3 12 (1983)), and there is a positive correlation between the number of bacteria present in a root canal and the incidence of interappointment flare-ups. The presence of black-pigmented, gram negative anaerobes in the root canal usually accompanies patient complaints of pain, swelling, and tenderness to percussion (Haapasalo, *FEMS Immunol. and Medical Micro.*, 6:213-217 (1993)). Thus, the successful elimination of bacteria from root canals may lower the incidence of flare-ups.

Antibiotics have historically been used as an adjunct to endodontic treatment either by systemic or local administration. Currently, antibiotic treatment for root canal infections and exacerbations is limited to systemic administration. Thus, in light of the established correlations between the primary and secondary effects of bacterial presence and the incidence of both interappointment flare-ups and treatment failure, there is a clear need for an efficacious method of delivering and sustaining substantial concentrations of intracanal medicaments, particularly antibiotics.

During the 1950's a polyantibiotic paste (PBSC) was devised for use as an intracanal medicament (Grossman, L. I., *J. Amer. Dent. Assoc.*, 43:265-278 (1951)). PBSC consisted of penicillin to target gram positive organisms, bacitracin for penicillin-resistant strains, streptomycin for gram negative organisms and caprylate sodium to target yeast, all suspended in a silicone vehicle. Although, clinical evaluation suggested that polyantibiotic paste conferred a therapeutic benefit (fewer treatments to achieve a negative culture) the composition was ineffective against anaerobic species (which are now appreciated as the dominant species responsible for treatment failure). In 1975 the Food and Drug Administration (FDA) banned PBSC for endodontic use primarily because of the risks of sensitization and allergic reactions attributed to the penicillin.

This underscores the importance of improving historical endodontic methodologies, particularly local delivery methods, in light of contemporary knowledge and technological advances.

SUMMARY OF THE INVENTION

The invention relates to endodontic fibers comprising a biocompatible polymer 20 vehicle which is permeable to medicaments, or combinations of medicaments, dispersed, e.g., homogeneously, therein. Such fibers can be used, for example, in a method for the local delivery and sustained release of medicaments to periodontal or intracanal treatment sites. Endodontic fibers of this invention include modified periodontal fibers and intracanal fibers.

One embodiment of the invention relates to modified periodontal fibers suitable for delivery of medicaments to intracanal treatment sites. These first generation endodontic fibers, referred to herein as "modified peridontal fibers", represent an adaptation of an ethylene vinyl acetate delivery vehicle (see U.S. Pat. Nos. 4,764,377 and 4,892,736) previously developed to administer therapeutic agents during the course of periodontal treatment (Gilad, "Development of a Clindamycin Impregnated EVA fiber as an Intracanal Medicament in Endodontic Therapy," Master of Medical Sciences Thesis, Harvard University School of Dental Medicine, defended Apr. 2, 1998, and Gilad, et al., "Development of a Clindamycin-Impregnated Fiber as an Intracanal Medication in Endodontic Therapy," Journal of Endodontics, 25(11):722-727 (1999), the entire teachings of which are incorporated herein by reference). Specifically, the periodontal fibers have been modified to confer properties which allow the use of the fiber within an intracanal treatment site, e.g., to confer specific physical characteristics such as form and consistency. In one embodiment, the modification comprises the treatment of the periodontal fiber with an agent such as a biocompatible refrigerant spray (e.g., Endo Ice).

In an alternative embodiment, the invention also relates to a second generation endodontic fiber, referred to herein as an "intracanal fiber," which can be specifically designed for use in intracanal delivery methods, thereby obviating the need to modify a peridontal fiber for use in intracanal sites. Such design can include an alteration in the composition and/or ratio of components of the fiber. For example, as described herein, it has been discovered that an ethylene vinyl acetate (EVA) fiber containing less than about 20% vinyl acetate is suitable for use as an intracanal fiber. In a preferred embodiment, the EVA fiber contains less than about 20%, preferably less than about 15% and more preferably less than about 10% vinyl acetate. In one embodiment, the EVA fiber contains about 9.3% vinyl acetate. In a preferred embodiment, the intracanal fiber has a diameter of less than about 0.5 mm. In one embodiment the intracanal fiber has a diameter of about 0.3 mm.

The invention is demonstrated herein using clindamycin/ethylene vinyl acetate (EVA) fibers; however, this example is not intended to limit the scope of the invention in any way. For example, the contemplated intracanal fiber can be formulated to have a polymeric composition, surface tackiness, stiffness, glass transition temperature, and/or diameter selected to confer characteristics compatible with placement within the root canal. Although the second generation intracanal fiber is particularly adapted for intracanal use, other (i.e., non-intracanal) uses of this fiber are also envisioned. For example, the intracanal fiber can also be used for periodontal treatment.

In addition, the choice of medicament and the dose at which it is incorporated 5 into the disclosed endodontic fibers (e.g., modified peridontal fibers or intracanal fibers) are optimized to produce a fiber that is most likely to achieve the desired therapeutic effect. The intracanal fibers exemplified and contemplated herein are ideally suited for the local delivery and sustained release of intracanal medicaments and thus enable numerous intracanal delivery methods.

In one aspect of endodontic use, endodontic fibers (e.g., modified peridontal fibers or intracanal fibers) are utilized for the intracanal delivery and sustained release of antibiotics predicted to be efficacious for the treatment of an established endodontic bacterial infection. The goal of the intracanal delivery of antibiotics in this context is to achieve a sufficient drug concentration and duration of contact, to effect inhibition (e.g., partial or complete inhibition) of all bacterial growth within the pulp chamber and root canal, thereby obviating the need for systemic antibiotic administration. Ultimately, the ability to successfully treat established bacterial infections will reduce endodontic treatment failures.

In an alternative embodiment, an intracanal delivery method using endodontic fibers of the invention is utilized prophylactically to disinfect a root canal receiving endodontic treatment prior to the application of a final restoration. In this context, the local delivery method is employed to eradicate any residual bacteria which were not removed by the chemomechanical preparation of the canal. More specifically, the purpose of this method of delivery is to suppress bacterial growth, particularly the proliferation of black-pigmented, gram negative organisms within the root canal. Such prophylaxis can reduce the level of patient pain due to inflammation and the occurrence of interappointment flare-ups, and ultimately minimize the risk of treatment failures.

In other embodiments of the invention, endodontic fibers described herein can be used to deliver alternative intracanal medicaments necessitated by a course of endodontic treatment. For example, in an effort to attenuate a host-mediated inflammatory response resulting from the presence of bacterial by-products in periapical tissues, an anti-inflammatory agent, either alone or in combination with an antibiotic, can be incorporated into the endodontic fiber.

DETAILED DESCRIPTION OF THE INVENTION

Figure 1:
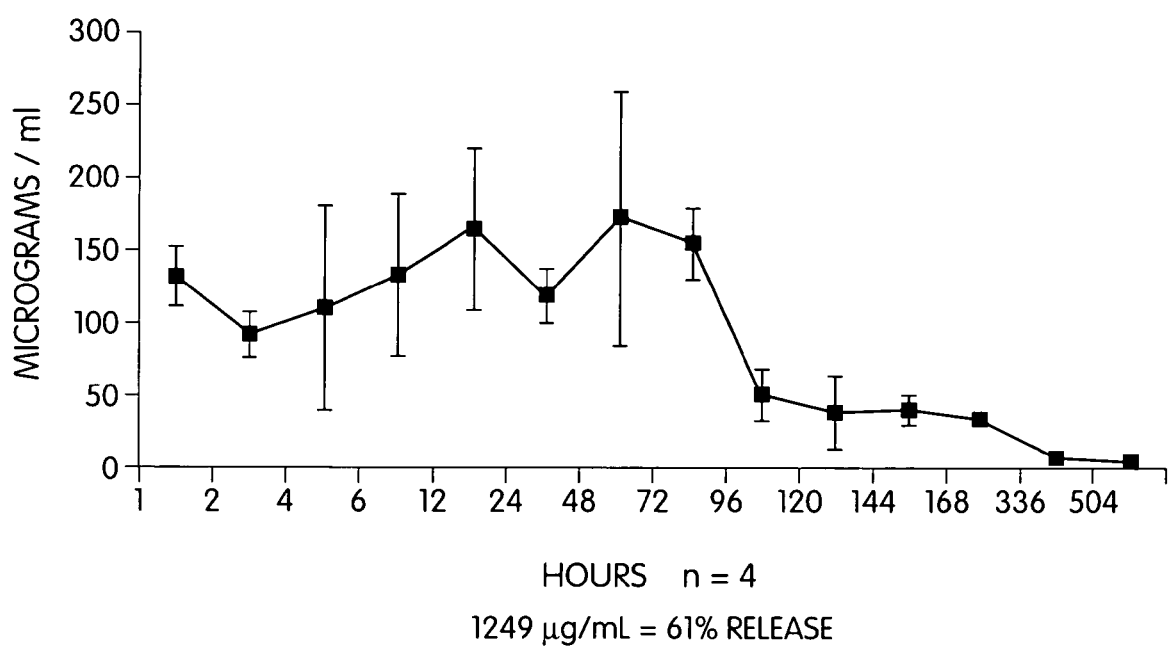
FIG. 1 is a bar graph indicating the number of colony forming units (CFUs) isolated from paper point or crushed teeth samples of extracted human teeth infected in vitro with *P. intermedia* and treated with either periodontal clindamycin/EVA fibers, or EVA control fibers.

The role of endogenous microflora as a source of bacterial infection contributing to endodontic treatment failure is well established (Kakehashi, S. et al., *Oral Surg.*, 20:340-348 (1965)). The bacterial species most often associated with infections of endodontic origin belong to the genera *Prevotella, Porphyromonas, Fusobacterium, Peptostreptococcus, Eubacterium* and *Streptococcus*. Some published studies have implicated species of black-pigmented, gram negative anaerobes as possible endopathogens (based on a frequency of isolation in the 25% to 50% range from teeth experiencing treatment failure), however, no single species has been proven to be more pathogenic than others (USAIDR Information Bulletin, 4(3) (1990)).

A "flare-up" is defined as pain and/or swelling which occurs within a few hours to a few days after a root canal treatment procedure. Depending upon the severity of the symptoms, there is often a sufficient disruption of the patient's lifestyle such that the patient initiates an unscheduled visit and treatment. Published studies suggest that the presence of members of the black-pigmented Porphyromonas (particularly *Porphyromonas gingivalis* and *Porphyromonas endodontalis*) within the root canal correlate with the type of acute symptoms responsible for inter-appointment flare-ups (Yoshida et al., J. Endodon., 13:24-28 (1987)). Thus, in addition to reducing the failure rate of endodontic treatment, it also desirable to reduce the frequency of interappointment flare-ups.

Antibiotics have historically been used as an adjunct to endodontic treatment, either by systemic or local administration. Currently, antibiotic treatment for root canal infections and exacerbations is limited to systemic administration. Commonly prescribed antibiotics include penicillins (e.g., penicillin V, amoxicillin), erythromycins (e.g., erythromycin stearate), lincosamides (e.g., clindamycin) and cephalosporins (e.g., cephalexin). The decision to use antibiotics is often made by the practitioner in relation to his or her own treatment philosophy. The choice is made in light of the knowledge that systemic antibiotics should be prescribed with restraint because of the possibilities of hypersensitivity or anaphylactic reactions, toxicity, adverse systemic effects, and the development of resistant strains of microorganisms.

A critical reevaluation of the merits of delivery devices, vehicles, techniques, and medicaments which have been historically utilized for intracanal delivery methods reveals that the use of intracanal medicaments in general, and in particular the use of intracanal antibiotics, has been criticized for inadequate spectrum of activity and short duration of effectiveness. The former issue has been addressed by improved microbiological sampling techniques, particularly anaerobic culturing techniques, which now provide practitioners with an accurate profile of the bacterial species associated with endodontic infections. This information enables practitioners to prescribe more appropriate antimicrobial agents. As a result, the short duration of effectiveness emerged as the major flaw of intracanal delivery protocols. The endodontic fibers described herein address this issue by allowing a treatment strategy which is demonstrated to be capable of the sustained release of active medicament for at least 14 days (in vitro).

The disclosed endodontic fibers enable a delivery system and method capable of the sustained release of any class of medicament that is necessitated as a consequence of therapy, particularly root canal therapy. In preferred embodiments, the invention provides a therapeutic method for the treatment of an endodontic bacterial infection, or alternatively a controlled aseptic technique suitable for use as an adjunct to conventional chemomechanical debridement and irrigation techniques.

Systemic administration relies upon circulatory elements to bring active drug to an infected site. However, it is well recognized that infected and/or inflamed periradicular tissue and necrotic pulpless teeth do not posses a normal vasculature. This practical consideration renders systemic administration inefficient, particularly when it is combined with the knowledge that to be effective, an antibiotic must be in contact with the targeted microorganisms. These facts clearly compromise the potential utility of systemically administered prophylactic antibiotics.

In contrast, a local delivery strategy confers the therapeutic benefit of delivering a medicament directly to the targeted tissue space. In addition, use of the disclosed delivery vehicle and method is readily amenable to both bacteriological sampling and sensitivity screening in the event that an infection does not respond to an initial course of treatment, and the easy removal of the fiber in the case of an unforeseen complication or allergic reaction. The latter feature represents a significant improvement over the historical use of paste or liquid compositions.

Furthermore, the ability to establish substantial local concentrations of an antibacterial agent also minimizes the risk of contributing to the development of drug resistant pathogens. One of the major contraindications to the use of systemic antibiotics is the theoretical possibility that bacteria not affected by the relatively low concentrations achieved by oral administration will give rise to strains having multiple drug resistance. Intracanal delivery also spares the patient from unwanted side-effects commonly associated with systemic administration strategies. For example, systemic clindamycin administration has been associated with the occurrence of pseudomembranous colitis, a sufficiently deleterious side effect which accounts for the reluctance of many clinicians to prescribe clindamycin, despite its broad spectrum of activity. However, given the dosages required to cause pseudomembranous colitis, along with the requirement for gastrointestinal contact, it is unlikely that the intracanal use of clindamycin/EVA endodontic fibers would trigger such an adverse side effect. This later benefit can be decisive in terms of prescribing a particular medicament whose spectrum of activity may be well suited for the task, but systemic administration carries a high risk of toxicity.

The intracanal fibers described herein are specifically designed for use in intracanal delivery methods. The optimal composition of the fibers can be empirically determined to confer the physical characteristics and polymeric composition required for intracanal use. The intracanal fibers can have a diameter of from about 0.1 mm to about 2.0 mm. In a preferred embodiment, the endodontic fiber has a diameter of from about 0.1 to about 0.5 mm; this particular diameter range facilitates placement deep within the cleaned and reshaped root canal. Most preferably, the intracanal fiber has a diameter of about 0.3 mm. Intracanal fibers suitable for use in the disclosed invention can further comprise additional features characteristic of the modified periodontal fibers exemplified herein. More specifically, particularly preferred fibers are characterized by additional features such as being odorless, being colorless, permitting deep penetration of the root canal, being suitable for use with a variety of therapeutic agents, being capable of the sustained release of at least one active agent (e.g., for at least a one week period of time (in vitro)), and not staining tooth structure or interfering with standard bacterial culture techniques.

The composition and glass transition temperature of the polymer can also be selected to confer surface characteristics and a level of rigidity required to accomplish the aseptic placement of the fiber within the root canal, and to facilitate the subsequent conformity of the fiber to the contours of the root canal. Biocompatible vehicles useful for the formulation of the disclosed endodontic fibers are biocompatible synthetic or natural copolymers, which may or may not be biodegradable. For example, polymers such as collagen, cellulosic polymers, glycolic acid polymers, methacrylate polymers, ethylene vinyl acetate polymers, ethylene vinyl alcohol copolymers, polycaprolactone, polyurethanes and polylactides and combinations thereof are suitable for use in this invention. The form (i.e., shape) of the polymer composition is not critical as long as the form allows the composition to be positioned within the root canal, preferably the positioning required is deep within the tooth canal to enable the medicament act locally at the site of deep bacterial infection. In a preferred embodiment the form of the polymer composition is a string or fiber. For example, polymers useful for the preparation of second generation intracanal endodontic fiber according to the invention contemplated herein are described in U.S. Pat. Nos. 4,764,377 and 4,892,736.

It is recognized that in the preparation of an endodontic fiber for use in an intracanal delivery method, certain inert substances may be included to further modify the delivery characteristics, or to serve as carriers of the active agent, including solvents, suspending agents, surfactants, viscosity-controlling agents, and other pharmaceutically acceptable materials which may be desirable to solubilize or stabilize the therapeutic agent (or agents) in the delivery vehicle, or to control the rate of permeation or the action of the agents after permeation.

According to the invention, the modified periodontal fiber or intracanal fiber is impregnated with one or more medicaments using methods known in the art. A wide variety of medicaments may be used in the invention, either alone or in combination. Therapeutic agents suitable for use in the invention include, but are not limited to: antibiotics such as clindamycin, tetracycline, neomycin, kanamycin, metranidazole or canamycin; antimicrobial agents such as iodine, sulfonamides, mercurials, bisbiguanidines, or phenolics; anti-inflammatory agents such as indomethacin or hydrocortisone; immune reagents such an immunoglobulins, or antigen binding fragments of immunoglobulins or immunomodulatory agents such as methotrexate.

In addition, it is recognized that in certain forms of therapy, combinations of these agents in the same delivery vehicle may be utilized in order to obtain an optimal effect. Thus, for example, an antibiotic and an anti-inflammatory agent may be combined in the preparation of a single endodontic fiber, which could be used either as an adjunct or a substitute for traditional endodontic treatment protocols.

The choice of medicament, and the dose at which it is incorporated into the endodontic fiber, can be selected to produce fibers that achieve the desired therapeutic effect, in light of a particular set of factors. For example, the initial selection of an appropriate antibiotic, and the dose at which incorporated into the endodontic fiber, are empirical choices guided by knowledge of the bacterial species commonly associated with treatment failure, the condition of the particular tooth receiving treatment, and the time span between scheduled appointments. Properties desirable in an ideal intracanal antibiotic or antimicrobial agent (or combination thereof) for use during root canal treatment are that the medicament be germicidal to all, or at least a portion of, organisms present at the treatment site, rapidly effective, capable of deep penetration into the canal system, effective in the presence of organic matter, noninjurious to periapical tissues, chemically stable, odorless, tasteless, and inexpensive. In practice, the selection of a therapeutic agent for use in the described intracanal delivery methods will be dictated by the permeability of the delivery vehicle to the agent, the dose at which the agent can be incorporated into the fiber, and the toxicity of the agent.

For example, clindamycin is effective against many of the bacterial taxa commonly associated with endodontic treatment, and depending on the effective concentration achieved at the site of infection it can be either a bacteriostatic or a bacteriocidal antibiotic. It is effective against: *Actinomyces, Eubacterium, Fusobacterium, Propionibacterium, microareophilic Streptococci, Peptococcus, Peptostreptococcus, Veillonella, Prevotella*, and *Porphyromona*. Also, hypersensitivity and anaphylaxis as a result of clindamycin exposure is extremely rare. In addition, data presented herein demonstrates that clindamycin/EVA intracanal fibers are active in vitro against the black-pigmented *Prevotella* and *Porphyromonas* species, which are commonly associated with the occurrence of flare-ups. Clindamycin binds exclusively to the 50S subunit of bacterial ribosomes and interferes with peptidyl transfer, which prevents elongation of peptide chains and ultimately suppresses bacterial protein synthesis. (AHFS Drug Information Reference, 388-393 (1997)). The minimum inhibitory concentration (MIC) of clindamycin for most susceptible aerobic and micoroaerophilic bacteria is 0.1-0.4 mg/mL, and is often observed to be much lower than the corresponding penicillin or erythromoycin MIC. Published studies indicate that over the twenty year period ending in 1986, there has been no marked change in the sensitivity of bacteria to lincomycins, and more specifically that 70% to 80% of all bacterial species isolated have remained susceptible to clindamycin. Conversely, a reduction in bacterial sensitivity, and in some instances evidence of resistance, has emerged among amoxicillin, cephalosporins, and erythromycin during the same period of time (Woods, *Aust. Dent. J.*, 33:420-423, 505-510 (1988)).

The use of the disclosed endodontic fibers and methods during the course of endodontic treatment can readily be adapted to complement a typical endodontic treatment program. Conventional root canal therapy is performed over a series of visits, to allow sufficient time to pass from the initial pulpectomy, chemomechanical debridement, and irrigation to ensure that the pulp chamber and root canal are aseptic prior to the application of the final restoration. Therefore, the anticipated use of the medicament-impregnated fiber in the context of either a prophylactic method, or for the treatment of an established infection, does not require, but could optionally utilize, a biodegradable polymer. The controlled release characteristic of the fiber, combined with the opportunity for periodic replacement, makes the method compatible with conventional endodontic treatment protocols, and increases the likelihood that the local administration will achieve its desired therapeutic effect.

The modified periodontal fiber and intracanal fiber claimed and described herein are suitable for use in any and all of the disclosed methods of intracanal delivery, including, but not limited to, prophylactic disinfection of the root canal, treatment of a bacterial infection, attenuation of a host-mediated inflammatory response, and the sustained delivery of an appropriate intracanal medicament necessitated by endodontic treatment.

The invention will now be further described by the following non-limiting 20 examples. The teachings of all literature, patents and published patent application referred to herein are incorporated herein in their entirety.

EXAMPLES

Periodontal Fibers

Preparation of a Periodontal Clindamycin/EVA Endodontic Fiber and in vitro Efficacy Against Endodontic Pathogens First generation (periodontal) clindamycin/EVA endodontic fibers were prepared according to a method used for the preparation of periodontal tetracycline/EVA fibers (as described in U.S. Pat. No. 4,892,736) with slight modifications. In brief, 0.075 g calcium phosphate monobasic ($CaH_2PO_4$) was combined with 10 mL distilled water ($dH_2O$) and added to a solution consisting of 0.050 g clindamycin phosphate and 10 mL $dH_2O$. The combined solution was then lyophilized for 24 hours. The resultant powder was filtered through a #325 mesh sieve (W.S. Tyler Co., Mentor, Ohio) in order to achieve uniform particle size of 45μ. The resultant yield (125 mg) was combined with 375 mg of EVA particles (USi Inc., TN) and processed through an extrusion plastometer (Tinius Olsen Co., Willow Grove, Pa.) at diameters of 2.0 mm, 1.0 mm, and 0.5 mm. The final extrusion produced a 250 mm long fiber, with a calculated approximate dose of 2.0 mg clindamycin/10 mm fiber.

Bacterial sensitivity to the modified peridontal clindamycin/EVA fiber was determined by placing 10 mm long fiber segments of on blood agar plates colonized by the following bacterial species: *F. nucleatum* (ATCC 364), *P. intermedia* (ATCC 25621), *P. micros* (ATCC JH20), *S. intermedius* (ATCC 27335), *P. endodontalis* (ATCC 35406), *P. gingivalis* (ATCC 381), *P. melaninogenica* (ATCC 25845), *E. lentum* (ATCC 25559), *V. parvula* (ATCC 10790), *S. sanguis* (ATCC 551), *P. buccae* (ATCC 33574), *P. oralis* (ATCC 33269), or *P. acnes* (ATCC 11827). Assay plates were incubated in anaerobic chambers for four days prior to the measurement using a millimeter ruler and recording of the resulting zones of inhibition. Table 1 summarizes the observed zones of inhibition. Control fibers, consisting of EVA fibers without clindamycin, failed to produce any detectable growth inhibition of the above-listed bacterial species. These data demonstrate that periodontal clindamycin/EVA fibers have significant antimicrobial activity against endodontic microorganisms.

Table 1

Assessment of Periodontic Fiber Effectiveness Versus Endodontic Bacteria in Vitro In vitro Suppression of Bacterial Growth in Extracted Human Teeth Infected with Endodontic Pathogens by Periodontal Clindamycin/EVA Fibers To test the efficacy of the periodontal clindamycin/EVA fibers an in vitro assay was developed based on the use of extracted human teeth which are persistently infected with endodontic pathogens. Thirty-two extracted human teeth (anteriors/premolars) were sectioned at the cementoenamel junction, shaped with 0.04 taper nickel-titanium rotary endodontic instruments (Tulsa Dental, Tulsa, Okla.) and fully cleaned with 5.25% sodium hypochlorite (NaOCl), followed by thorough flushing with distilled water. The smear layer was not removed. The teeth were then sterilized by autoclaving for 20 minutes and coated with sticky wax, leaving the apical foramen and coronal orifice patent.

In initial studies *P. intermedia* was grown on blood agar plates and was used as the infecting microorganism. BBL Mycoplasma broth was prepared by sterilizing a solution consisting of 1.05 g of BBL mycoplasma broth powder with 0.1 g glucose, 0.5 15 g hemin, 50 mL $dH_2O$ and 0.025 g L-cysteine (at pH 7.4-7.6). Under nitrogen influx, tubes of sterile broth were combined with *P. intermedia* colonies from the stock agar plates, and diluted to a concentration of $10^9$ bacteria/mL (optical density reading of 1.0@600 nm), and then diluted to $10^6$ bacteria/mL by adding 50 μL of bacterial broth to 450 μL sterile media. The sterile teeth were then introduced into tissue culture wells filled with the bacterial broth. The wells were lightly covered and placed in an anaerobic chamber for four days.

For sampling purposes, the teeth were moved into dry wells, and sterile paper points were inserted for 15 seconds. The resulting sample was then dispersed by vortexing to release the sample microorganisms into 1 mL aliquots of sterile media. 25 Ten-fold serial dilutions were performed by transferring 50 μL of bacterial broth into 450 μL of sterile media under nitrogen influx for $10^{-2}$, $10^{-3}$ and $10^{-4}$ concentrations. 100 μL samples were spread onto blood agar plates, and cultured for four days under anaerobic conditions. On the fifth day the teeth were transferred into a second plate containing 500 μL of fresh media and returned to anaerobic culture conditions for an additional 4 days. After eight days, paper point sample plates corresponding to teeth exhibiting positive growth were quantified for number of colony forming units (CFUs) and two teeth had to be eliminated from the study due to lack of bacterial colonization. Seven colonized teeth were randomly selected for use as control teeth (receiving 10 mm long EVA fibers formulated without any antibiotic), and seven other infected teeth were utilized as experimental teeth (receiving 10 mm long periodontal clindamycin/EVA fibers). Periodontal clindamycin/EVA fibers were prepared as described above, and to facilitate fiber manipulation and insertion they were treated to decrease their surface tackiness and increase their rigidity by spraying with a biocompatible refrigerant spray (such as Endo Ice) thereby producing "modified periodontal fibers."

Following fiber placement the teeth were placed into new wells with 500 μL of fresh sterile media and returned to anaerobic culture conditions. Wells were replenished with fresh media daily for four days, at which point the teeth were sampled with paper points and assayed for bacterial colonization according to the serial dilution and plating method described above. To ensure the detection of bacterial species colonizing locations which are theoretically not accessible paper point sampling (such as complex anatomical spaces in the root canal system, or dentinal tubules) entire teeth were individually fractured and crushed in sterile autoclave bags and then dispersed into culture tubes containing 1 mL sterile media. Crushed-tooth samples were serially diluted and plated according to the method described above for the paper point samples. CPUs from the suitably diluted blood agar plates were quantified 7 days later. Colony identification was verified by morphometric analysis. Statistical analysis of the differences observed between control (EVA fibers without antibiotic) and experimental (periodontal clindamycin/EVA fibers) were evaluated with the non-parametic Wilcoxin Rank Sum Test.

The data in FIG. 1 demonstrate that periodontal clindamycin/EVA fibers are efficacious in suppressing bacterial growth in teeth infected with *P. intermedia*. All seven experimental teeth treated with periodontal clindamycin fibers demonstrated no growth from either paper point or crushed tooth samples, demonstrating the efficacy of the fiber. In contrast, six of seven control teeth that received EVA fibers demonstrated positive growth. Statistical analysis utilizing the Wilcoxin rank sum test revealed no differences between baseline infected teeth with respect to CPU quantification prior to fiber placement ($p>0.05$). Samples from both paper point and crushed experimental teeth treated with periodontal clindamycin/EVA were significantly different from control teeth ($p<0.05$).

In a second experiment, the ability of periodontal clindamycin/EVA fibers to reduce bacterial infection with a mixed inoculum was assessed. Sixteen new teeth were prepared as described above, and placed into tissue culture wells containing 350 μL sterile media, and a mixture of 50 μL *F. nucleatum*, 50 μL *P. micros* and 50 μL *P. intermedia* at a concentration of $10^9$ bacteria/mL. Paper point samples were once again taken after four days to confirm and quantify bacterial growth. Modified peridontal fibers, prepared according to the method described above, were placed in 16 teeth for four days (eight controls and eight experimental), and the teeth were transferred into wells of fresh media daily. After obtaining paper point samples the teeth were crushed and serially diluted samples were prepared, and plated as described above.

Figure 2:
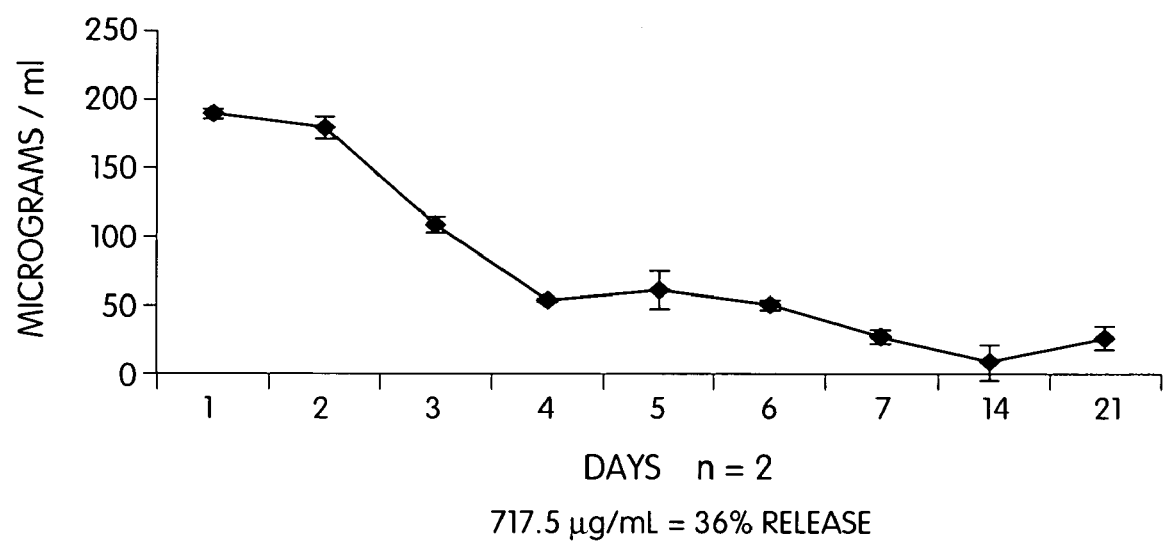
FIG. 2 are bar graphs indicating the CFUs isolated from extracted human teeth infected in vitro with a mixed inoculum of *F. nucleatum, P. micros*, and *P. intermedia* and treated with either periodontal clindamycin/EVA fibers or EVA control fibers. The graphs summarize clindanycin activity against each of the three species of bacteria present in the inoculum.

One week following fiber placement, the CFU load was quantified and compared with baseline CPU counts. Colony identification was again verified by morphometric analysis. Wilcoxian rank sum tests revealed that the differences between control and experimental teeth were all statistically significant ($p<0.05$). When comparing individual teeth for pre-treatment and post-treatment CFU values by t-Test, *F. nucleatum* groups were significantly different ($p<0.05$) as were *P. intermedia* groups ($p:<0.05$). However, the differences between the *P. micros* control and experimental groups were not significant ($p>0.05$). Thus, as shown in FIG. 2, the intracanal delivery of clindamycin was most effective against *P. intermedia*, less effective against *F. nucleatum*, and apparently ineffective against *P. micros* in the context of a mixed inoculum, despite the fact that clindamycin inhibits the growth of pure cultures of *P. micros* on blood agar plates.

In vivo Suppression ofBacterial Growth in Auto-Infected Root Canals of Ferret Canine Teeth by Periodontal Clindamycin/EVA Fibers Ferret canine teeth have been utilized successfiilly in endodontic research to study the induction of periapical lesions (Fouad, *Endo. and Dent Trauma*, 8:56-62 (1992)). The canine teeth are long and large enough to accommodate periodontal endodontic fiber placement, and therefore, can provide an in vivo model system to evaluate the ability of periodontal clindamycin endodontic fibers to inhibit bacterial growth in auto-infected root canals. Briefly, eight male ferrets (12 weeks old, approximately 3 lbs. each, Marshall Farms, Rose, N.Y.) were utilized to evaluate the in vivo efficacy of periodontal clindamycin/EVA fibers. Ferrets were premedicated with atropine (0.04 mg/kg, subcutaneously) 30 minutes prior to the procedure. Animals were then anesthetized intramuscularly with ketamine HCl (30 mg/kg) and xylazine (3 mg/kg) in sterile PBS. This anesthetic treatment was supplemented with a repeat dose of ketamine and xylazine when necessary. The pulp cavity of thirty two ferret canine teeth (4 teeth per each of 8 animals) was surgically exposed (using a #2 round bur and a high speed handpiece). Working lengths were confirmed radiographically. The root canal system was instrumented with 0.04 taper nickel-titanium rotary endodontic instruments to approximately a 0.30 mm apical preparation and irrigated with sterile saline. The teeth were left open for seven days to allow for bacterial colonization from the oral cavity. The auto-colonized teeth were subsequently closed with a cotton pellet and Intermediate Restorative Material (IRM) for a period of 14 days to allow for anaerobic bacterial growth and the development of pathogenesis. The teeth were then reopened (under general anesthesia) for modified peridontal fiber placement. Four of the eight animals received experimental periodontal clindamycin/EVA fibers (four teeth/animal) and the remaining four animals received negative control/EVA fibers. The teeth were resealed with cotton and IRM.

Treatment efficacy was determined seven days later after preparing crushed tooth samples from the treated animals. Briefly, the animals were placed under anesthesia, their mouths were swabbed with iodine and alcohol, the teeth were extracted intact and surface sterilized with iodine and alcohol, before being crushed inside of sterile autoclave bags. The fibers were subsequently removed, and the tooth fragments were placed into 1 mL of prereduced anaerobically-sterilized (PRAS) transport medium under nitrogen influx and immediately transported to the laboratory for serial dilution and plating under nitrogen influx as described in the in vitro studies above. Although the ferret canine teeth were generally long enough to accept and accommodate the fibers, they were sufficiently curved to complicate the extraction process. As a result some of the teeth were fractured and had to be excluded from the study.

Samples were serially diluted and incubated on blood agar plates in an anaerobic environment for seven days, and CFUs were quantified. Resultant data are presented in A, of FIG. 3. The average CFU count observed for control teeth (EVA fibers only) is $5.19 \times 10^5$ CPUs compared to an average of $1.89 \times 10^5$ CPUs for the experimental teeth (periodontal clindamycin/EVA fibers). This represented a 2.75-fold decrease in CPU load in the clindamycin treated teeth. The Wilcoxin rank sum test confirmed that the differences between control and experimental groups were statistically significant ($p<0.05$).

In a second experiment, two ferrets (one control and one experimental animal) were utilized. The control animal had four teeth treated with modified peridontal EVA fibers containing no clindamycin and a fifth tooth, neither accessed nor instrumented, but ultimately extracted, crushed, and sampled. The experimental animal had three teeth receiving modified peridontal clindamycin/EVA fibers and a fourth tooth treated with a modified peridontal tetracycline/EVA fiber. Paper point and crushed tooth samples were prepared as described above; however, two teeth were fractured upon extraction, and were not included in the data set.

Figure 3:
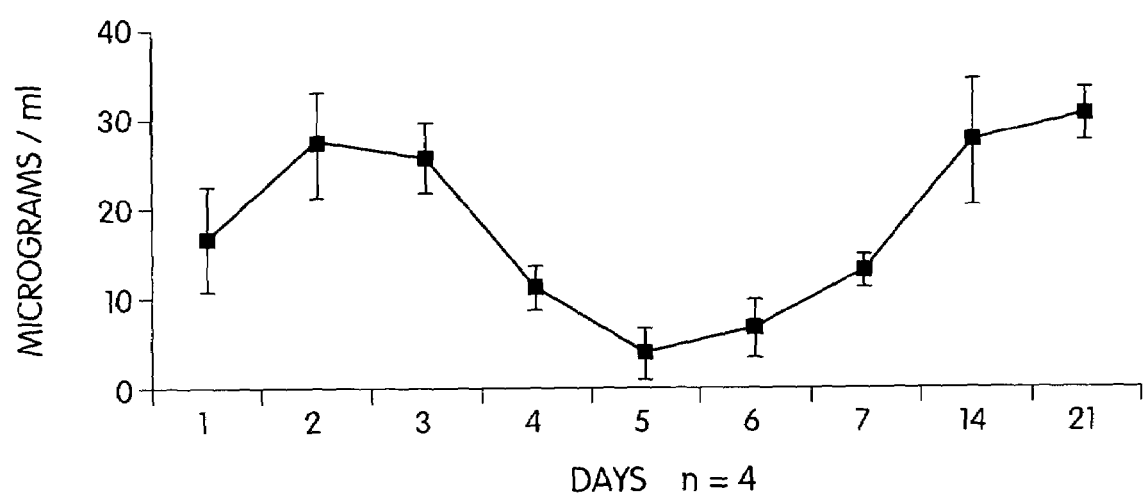
FIG. 3 are bar graphs summarizing the CFU load recovered from auto-infected ferret canine teeth undergoing root canal therapy, treated with either periodontal clindamycin/EVA fibers or EVA control fibers.

The resultant data are summarized in B, of FIG. 3. Due to the small sample, statistical analysis was not employed. Nonetheless, the experimental teeth showed a 6.3-fold decrease in CPU load when quantified from paper point samples, and a 4.3-fold decrease from crushed samples when compared with controls. The periodontal tetracycline/EVA fiber appeared to possess similar efficacy to that of the clindamycin fiber. The unaccessed control tooth showed no bacterial growth, establishing that the tooth isolation technique did not result in any contamination from the external root surface.

DNA-DNA hybridization checkerboard analysis as described by Socransky et al., *Biotechniques*, 17:788-792 (1994), was performed, using samples harvested from blood agar plates following one week of growth from both of the above in vivo experiments. The proportion of teeth colonized with each bacterial taxa was evaluated (presence vs. absence). Summary data compares control (EVA fiber only) versus experimental (periodontal clindamycin/EVA- or periodontal tetracline/EVA-treated) teeth. The data indicate that the treatment of teeth with periodontal clindamycin/EVA fibers does not favor the development of a unique bacterial profile relative to the profile observed in control teeth receiving control fibers.

Intracanal Endodontic Fibers

Preparation of an Intracanal Clindamycin/EVA Endodontic Fiber

Clindamycin fibers were manufactured in a manner similar to that of the prototype Clindamycin/EVA fiber (Gilad, 1998). To improve its physical properties, different preparations of Ethylene Vinyl Acetate EVA (ELVAX®, DuPont, Wilimington, Del.) were combined (containing 18, 25,28 and 30% vinyl acetate) and processed through an extrusion plastometer (Tinius Olsen Co., Willow Grove, Pa.).

Most of the vinyl acetate concentrations produced a sticky soft fiber, lacking rigidity. ELVAX® grade 750 was chosen as the delivery vehicle because of its similar rigidity to gutta-percha and the lack of tackiness of the former prototype. The grade 750 contains a low percentage of vinyl acetate (9.3%). The decrease of vinyl acetate in an EVA preparation increases its stiffness. The new, smaller (0.3 mm) diameter was achieved by a custom laser-calibrated orifice to fit the extrusion plastometer. In brief, 50 mg of clindamycin phosphate powder (Sigma Chemical Co., St. Louis, Mo.) was filtered through a #325 mesh sieve (W.S. Tyler Co., Mentor, Ohio) to achieve uniform particle size of 45μ. The resultant particles were combined with 150 mg of EVA pellets, grade 750 (ELVAX®, DuPont, Wilmington, Del.) and were sequentially processed through modified extrusion plastometer at 140° C. yielding fibers with diameters of 2.0 mm, 1.0 mm, 0.5 mm, and finally 0.3 mm. The final extrusion produced a 325 mm long fiber, which was cut at 13 mm segments, containing an approximate dose of 2.0 mg clindamycin. These resultant intracanal fibers have the following improvements over periodontal fibers: increase in rigidity similar to traditional gutta-percha points, thus eliminating the need of a refrigerant spray prior to canal insertion, reduction in diameter from 0.5 mm to 0.3 mm, and maintenance of a 2.0 mg dose despite a reduction in diameter. The reduction in diameter allows the penetration of the fiber deeper into the root canal, possibly releasing antibiotic closer to the apex apical accessory canals.

Figure 4:
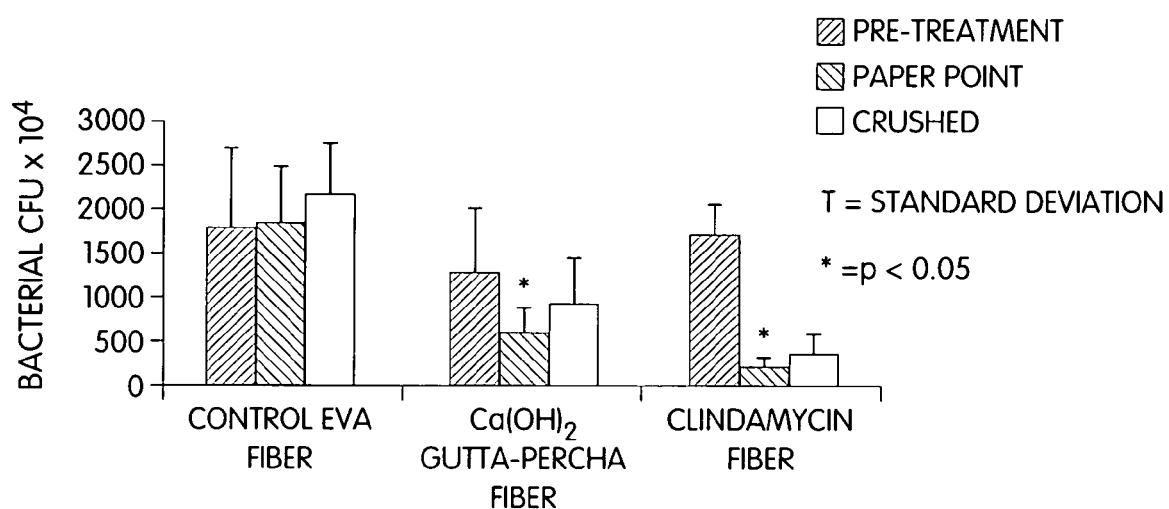
FIG. 4 is a graphic depiction of the kinetics of drug release from intracanal fibers.

Spectrophotometric Analysis of intracanal Clindamycin/ EVA and Ca (OH) J Guttapercha Release Clindamycin release from intracanal fibers was determined spectrophotometrically (1 mg/mL clindamycin equal to an optical density reading of 1.0@218 nm). Pour fibers were placed individually in sterile Eppendorf tubes containing 1 mL of PBS at 36° C. to determine antibiotic kinetic release. Samples were obtained after one hour and transferred with sterile cotton pliers to a new tube containing 1 mL PBS at the following time intervals: 2, 4, 6, 12 hours; 1, 2, 3, 4, 5, 6, 7, 14 and 21 days (as shown in FIG. 4). The results showed an initial mean release of 132.5 μg/mL at 1 hour, a maximum mean release of 175.5 μg/mL at 48 hours, and a gradual decrease to a mean release of 2.5 μg/mL at 21 days. The total amount of clindamycin released under these conditions to day 21 was 1249 μg/mL, about 61% of the total drug in the fiber.

Figure 5:
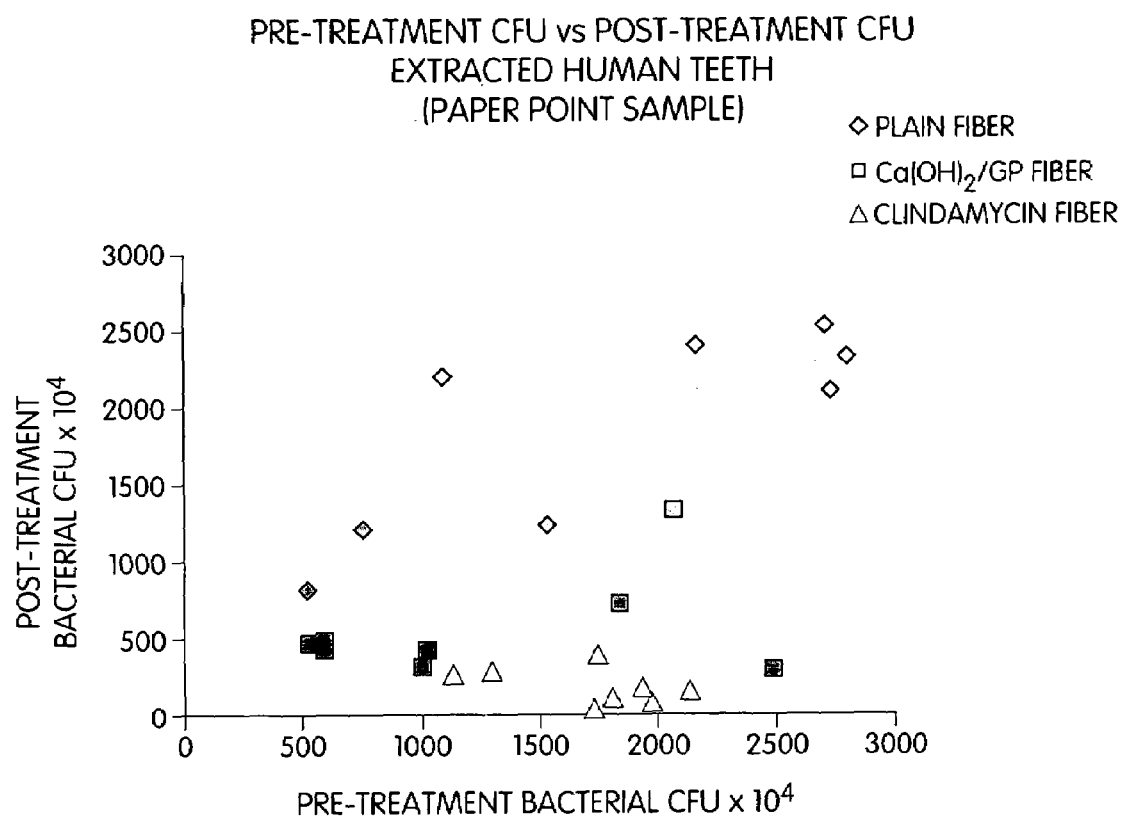
FIG. 5 is a graphic depiction of the kinetics of drug release from intracanal fibers.

In another experiment, two intracanal clindamycin/EVA fibers were similarly assessed after 1, 2, 3, 4, 5, 6, 7, 14 and 21 days. The clindamycin content of samples was determined spectrophotometrically with reference to the standard. Clindamycin release characteristics of Ca(OH)$_2$/Guttapercha points (Roeko, Langenau, Germany) were also determined. Ca(OH)$_2$/Gutta-percha points (ISO #25) measuring 13 mm from the tip were analyzed spectrophotometrically at the following time intervals: 1, 2, 3, 4, 5, 6, 7, 14 and 21 days at 36° C. (1 mg/mL in PBS equals optical density reading of 1.0@719 nm. The results (FIG. 5) showed an initial maximum mean release of 189.5 μg/mL at 1 day, gradually decreasing to 62 μg/mL at day 5 and subsequently declining to 9 μg/mL at day 14. Interestingly, on day 21, there was a slight increase observed to 26 μg/mL. The total release of clindamycin between day 1 and day 21 was 717.5 μg/mL, about 36% of the total amount of drug in the fibers.

These results suggest that clindamycin release decreases when the concentration of the drug in the external environment is high, and increases when the concentration is low.

Figure 6:
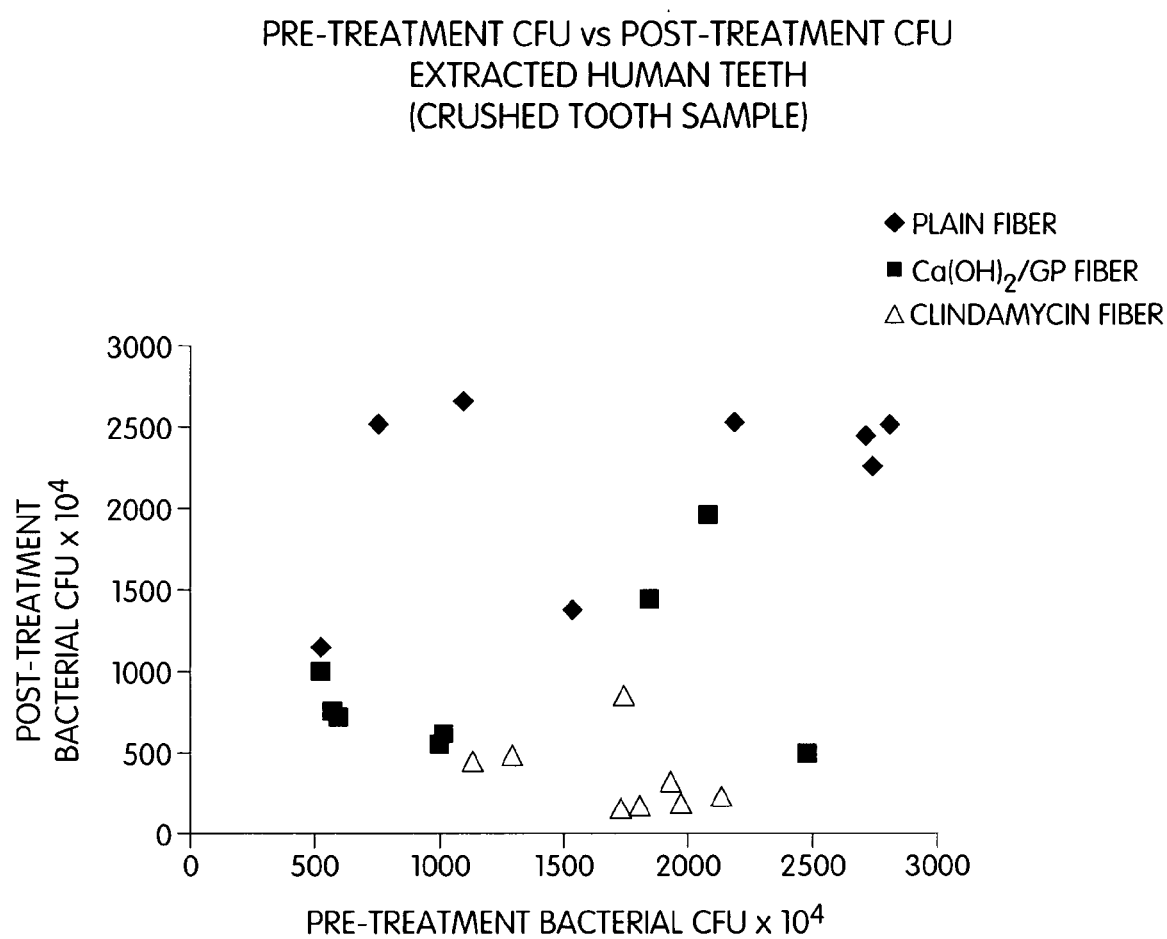
FIG. 6 is a graphic depiction of the kinetics of drug release from calcium hydroxide/gutta-percha points.

The release characteristics of Ca(OH)$_2$/gutta-percha points were analyzed at 1, 2, 3, 4, 5, 6, 7, 14 and 21 days. As shown in FIG. 6, the initial mean release was 16.5 μg/mL on day 1 and a maximum mean release at day 2 and 3 (27.75 and 25.75 μg/mL respectively), a decrease to 4 μg/mL at 5 days and a gradual increase to 30.25 μg/mL at day 21. The total mean release between day one and day 21 was 162.5 μg/mL Determination of Bacterial Sensitivity The bacterial sensitivity to the clindamycin fiber was established by placing 13 mm×0.3 mm diameter fiber segments on blood agar plates colonized by the following common endodontic microbes: F. nucleatum (ATCC 364), P. intermedia (ATCC 25621), P. micros (ATCC JH20), S. intermedius (ATCC 27335), P. gingivalis (ATCC 381), S. sanguis (ATCC 551), P. acnes1 (ATCC 11828). The fibers were handled with sterile cotton pliers. Controls consisted of EVA fibers without clindamycin. The plates were then placed into an anaerobic chamber after four days, and zones of inhibition were measured with a millimeter ruler and recorded. Similar evaluations were simultaneously conducted with a 13 mm (ISO #25) Ca (OH) 2/Gutta-percha point (Roeko, Langenau, Germany), a 13 mm premixed paste extrusion of calcium hydroxide (Pulpdent, Brookline, Mass.), and a control 13 mm EVA fiber as a negative control. The intracanal fibers produced varying degrees of inhibition. P. intermedia, p. gingivalis and F. Nucleatum demonstrated the greatest susceptibility to the intracanal fibers; while S. sanguis and P. acnes demonstrated intermediate susceptibility. Conversely, control EVA fibers, Ca(OH)$_2$ premixed paste (Pulpdent) and Ca(OH)$_2$ Gutta percha points did not generate any inhibition of any organism. These data demonstrate that intracanal clindamycin/EVA fibers have significant antimicrobial activity against most endodontic microorganisms. Table 2 summarizes the zone of inhibition.

Table 2

Zones of Inhibition of Bacterial Growth Induced by Intracanal Medic aments

In vitro Model to Evaluate Fiber Efficacy

To test the efficacy of clindamycin/EVA fibers in reducing bacterial growth in infected human root canals in vitro, a model was developed to persistently infect extracted human teeth with endodontic pathogens. Twenty-four extracted human teeth, (anteriors and premolars) were sectioned at the cementoenamel junction, fully instrumented and shaped with 0.06 taper nickel-titanium rotary endodontic instruments (Tulsa Dental, Tulsa, Okla.) at approximately 0.3 mm apical preparation, leaving the apical foramen and coronal oriface patent. Teeth were irrigated with 5.25% sodium hypochlorite (Na)CL followed by thorough flushing with distilled water. The smear layer was not removed. The teeth were then sterilized by autoclaving for 25 minutes. The teeth were divided into three groups of eight teeth each as follows: (1) Control (EVA alone); (2) calcium hydroxide gutta-percha point; and (3) intracanal clindaymycin/EVA fiber.

Figure 7:
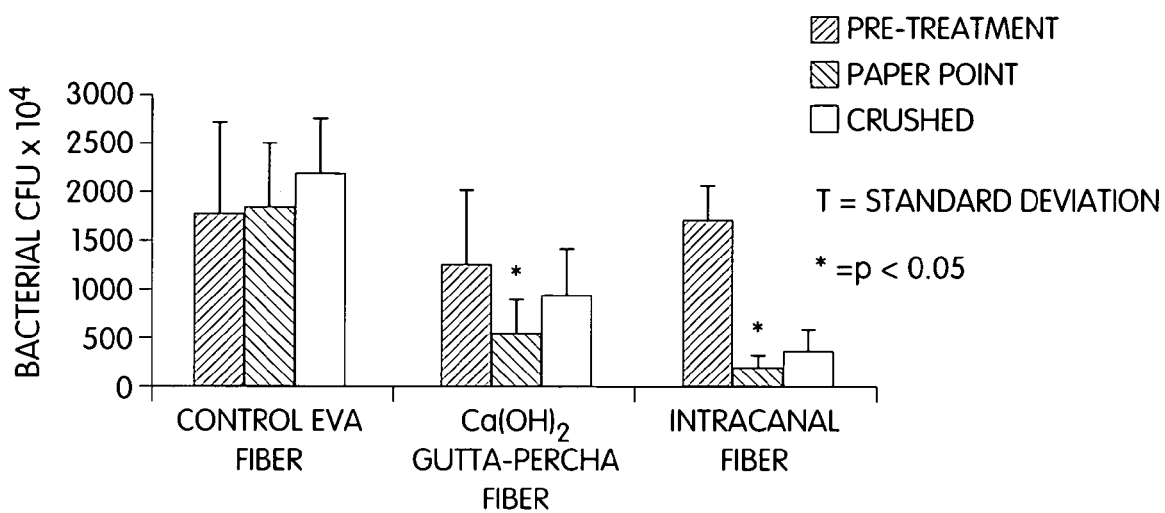
FIG. 7 is a graphic comparison of antibacterial activity of intracanal fibers vs calcium hydroxide/gutta-percha points in extracted human teeth.
Figure 8:
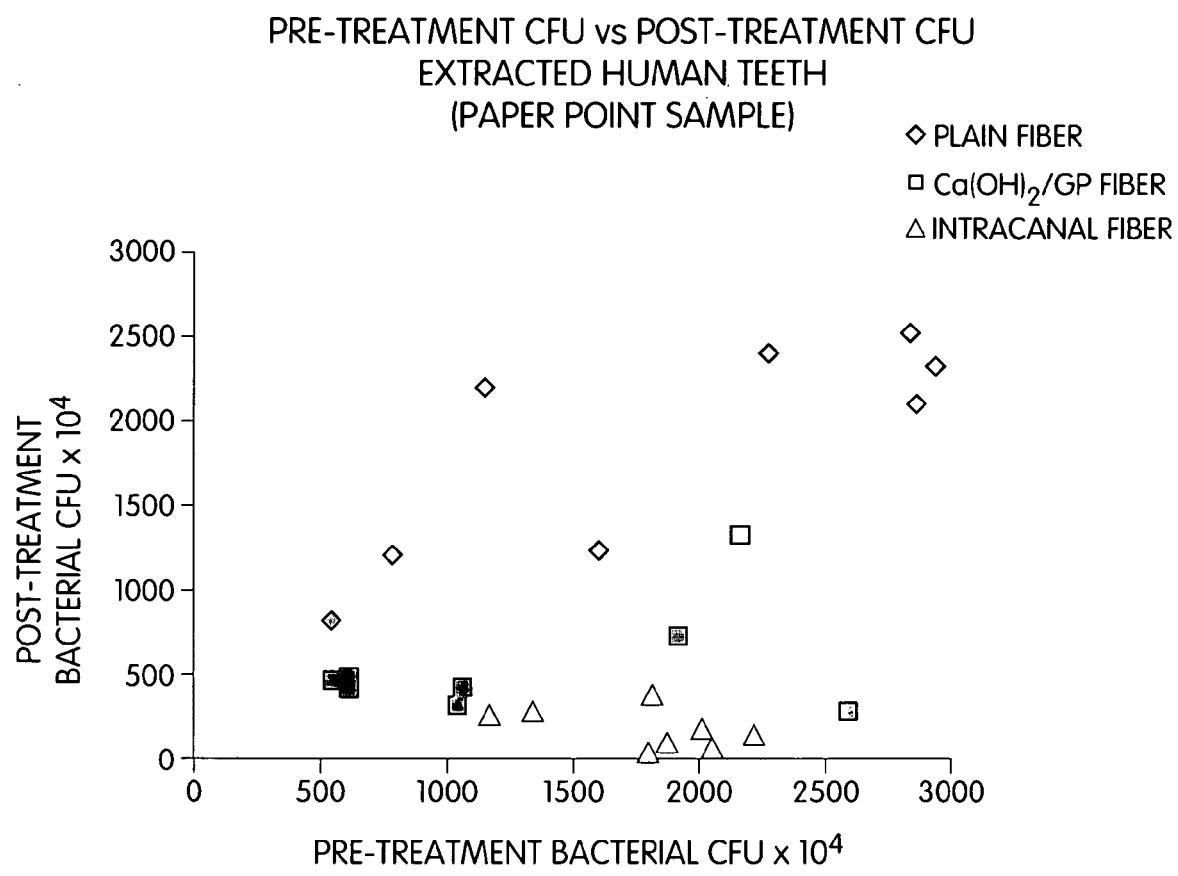
FIG. 8 is a graphic depiction of pre-treatment CFU versus post-treatment CPU in extracted human teeth (paper point samples).
Figure 9:
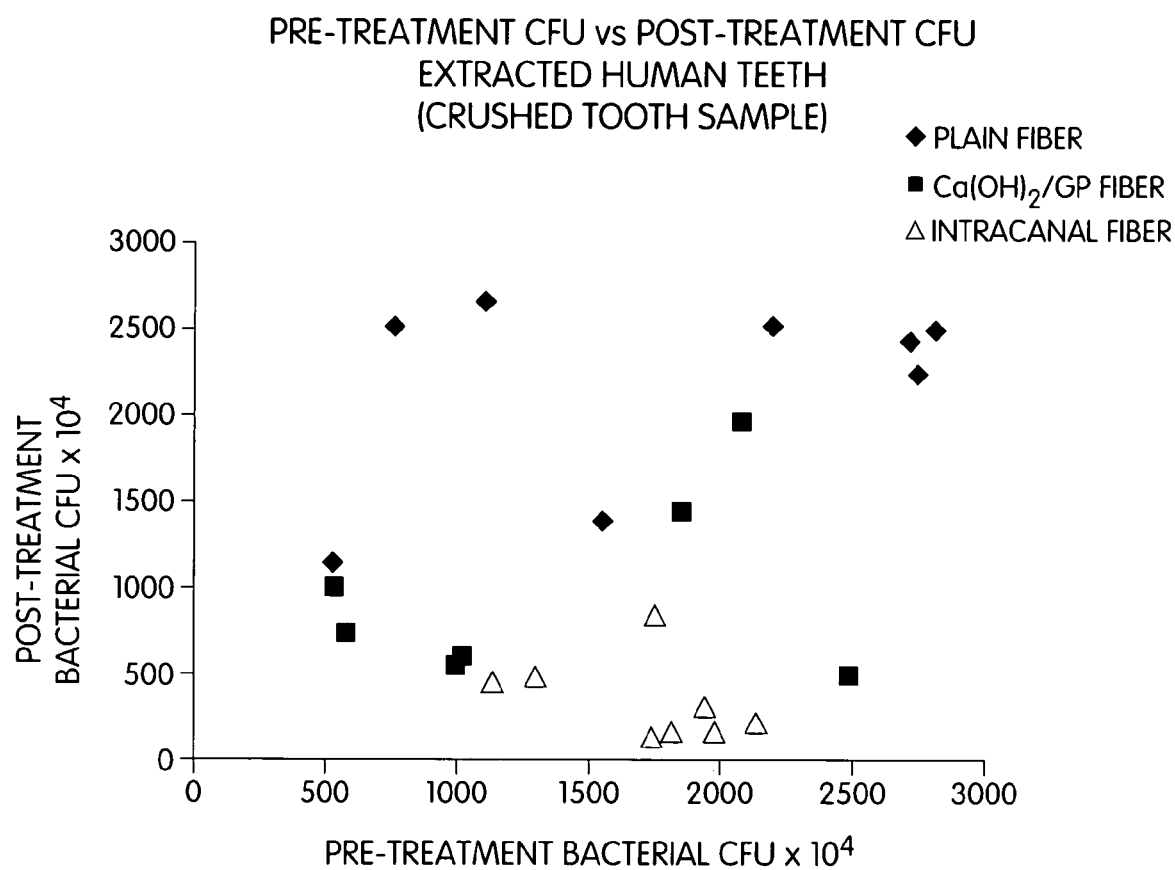
FIG. 9 is a graphic depiction of pre-treatment CPU versus post-treatment CFU in extracted human teeth (crushed teeth samples).

Under nitrogen influx, four flasks of sterile broth were each combined, with P. intermedia, P. micros, S. intermedius and F. nucleatum colonies from approximately 3×8 mm longitudinal slices of the stock agar plates. Each flask contained 25 mL of sterile BBL mycoplasma broth. The four flasks were maintained in an anaerobic chamber and were transferred daily to four flasks containing 100 mL, and 500 mL producing a total of 625 mL of inoculated BBL Mycoplasma broth. At the end of the experiment, 500 mL of the inoculated broth was centrifuged at 9000 rpm for 20 minutes. The supemanants were removed and each of the four pellets were diluted to a concentration of $10^9$ bacteria/mL (optical density reading of 1.0@600 nm), and then diluted to $10^8$ bacteria/mL by combining the inoculated broth with sterile prereduced anaerobically sterilized transport medium (PRAS), all under nitrogen influx. The sterile teeth were then introduced into sterile tissue culture wells (Coming Inc. Coming, N.Y.) containing 600 μL of sterile broth, and a mixture of 100 μL of F. nucleatum, 100 μL of P. micros, 100

μL of *F. intermedia* and 100 μL of *S. intermedius* at a concentration of $10^8$. The teeth were covered and placed in an anaerobic chamber for four days to allow for bacterial growth. Control fibers (EVA alone), calcium hydroxide/gutta-percha points or the intracanal clindamycin/EVA fibers were placed in each group of teeth. The teeth were replaced into fresh wells with 500 μL of sterile media, covered and incubated in the anaerobic chamber. The wells were replenished with sterile media every day until the next sampling (four days). The paper point samples were dispersed and vortexed in 1 mL of sterile PRAS transport medium under nitrogen influx. Ten-fold serial dilutions were performed by transferring 100 μL into 900 μL of (PRAS) under nitrogen influx for $10^{-2}$, $10^{-3}$ and $10^{-4}$ dilutions. Finally, 100 μL samples were spread onto blood agar plates, and allowed to grow for five days under anaerobic conditions. The CPUs were quantified under light microscopy using a grid. Pour days after the placement of the delivery systems, the teeth were paper point sampled and assessed by serial dilution. To ensure that no bacterial were missed from complex anatomical spaces in the root canal system or from dentinal tubules, the teeth were individually fractured and crushed in sterile PRAS. Ten fold serial dilutions were performed as detailed above from the paper point samples and the crushed teeth samples. The CPUs from the diluted blood agar plates were quantified 7 days later. Statistical Analysis was determined between test groups in the in vitro model utilizing extracted human teeth using the ANOVA method and the Tukey's studentized range test. The ANOVA method revealed that there were no significant differences in infection levels at baseline prior to fiber placement (p=0.31134). However, after treatment both paper point and crushed experimental teeth treated with intracanal fibers has a statistically significant reduction in infection levels at 4 days post-treatment (p=0.0001) (FIGS. 7, 8, and 9) A statistically significant reduction was also noted for the $Ca(OH)_2$ gutta-percha group compared to the control group, although this was not as profound as the reduction by the intracanal fibers (FIG. 7). The intracanal fibers had the largest mean reduction (1515.8 CFUs), which is statisticall'significant from the $Ca(OH)_2$ gutta-percha group (701.6 CFUs) with (p<0.05). The Tukey's studentized range test also showed that the difference in post-treatment CFUs between the intracanal fiber group and the $Ca(OH)_2$ gutta-percha group was not statistically significant.

In vivo Suppression ofBacterial Growth in Auto-Infected Root Canals of Ferret 25 Canine Teeth by Intracanal Clindamycin/EVA Fibers A similar protocol to the periodontal in vivo study detailed above was conducted. Briefly, teeth from six ferrets were utilized into four treatment groups. The groups were control/EVA fibers, clindamycin/EVA intracanal fibers, Roeko® fibers and calcium hydroxide paste.

The ferrets were infected with a mixture of four common endodontic pathogens, including *Streptococcus intermedius, Fusobacterium nucleatim, Peptostreptococcus micros,* and *Prevotella intermedia.*

Figure 10:
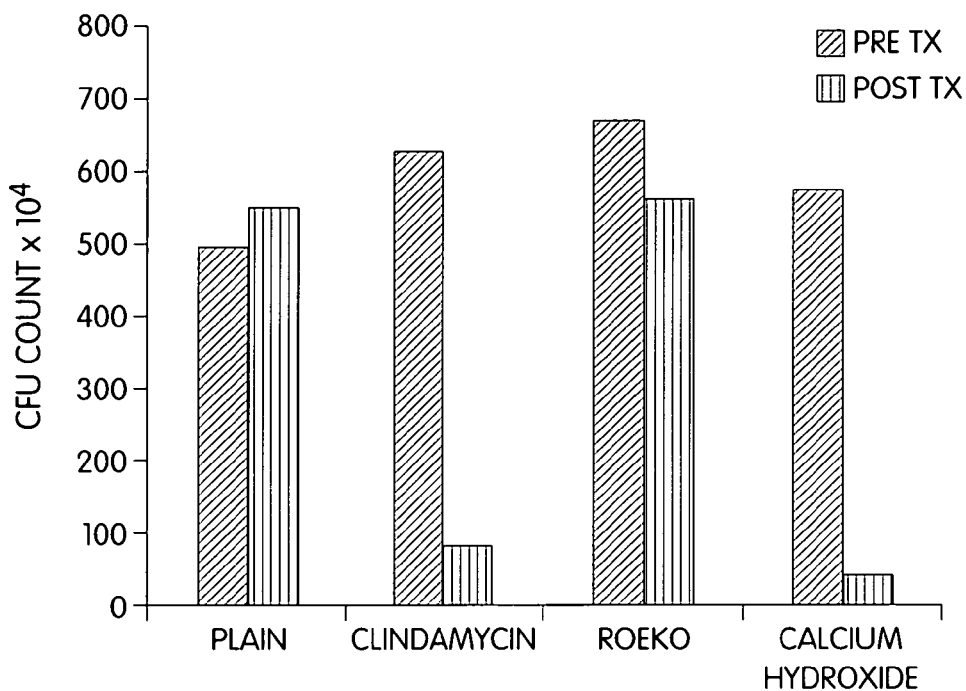
FIG. 10 is a graphic depiction of the pre-treatment CFU versis post-treatment CPU in a ferret animal model (paper point samples).

To analyze the residual infection, paper point samples were taken, the teeth were extracted and then crushed to release all bacteria within the root canals. The results are shown in FIG. 10.

While this invention has been particularly shown and described with reference to preferred embodiments thereof, it will be understood by those skilled in the art that various changes in form and details may be made therein without departing from the scope of the invention encompassed by the appended claims.

What is claimed is:

1. An endodontic fiber suitable for the local delivery and sustained release of one or more medicaments incorporated therein to an intracanal treatment site, comprising a polymer vehicle having incorporated therein one or more medicaments, wherein said endodontic fiber is capable of being positioned deep within a root canal to enable said one or more medicaments to act locally at a site of deep bacterial infection and wherein said endodontic fiber comprises a dose of said one or more medicaments of about 2.0 mg to about 5.0 mg per 10 mm of fiber.

2. The endodontic fiber of claim 1, wherein the medicament is selected from the group consisting of antibiotics, anti-inflammatory agents, antimicrobial agents, immune reagents, immunomodulatory agents, and combinations thereof.

3. The endodontic fiber of claim 2, wherein the medicament is an antibiotic selected from the group consisting of clindamycin, tetracycline and combinations thereof.

4. The endodontic fiber of claim 2, wherein the medicament comprises a combination of an antibiotic and an anti-inflanunatory agent.

5. The endodontic fiber of claim 1, wherein the polymer vehicle is an ethylene vinyl acetate copolymer having a diameter of from about 0.1 mm to about 2.0 mm and the medicament is clindamycin incorporated at a dose of about 2.0 mg to about 5.0 mg per 10 mm of fiber.

6. The endodontic fiber of claim 1, wherein said polymer vehicle comprises an ethylene vinyl acetate copolymer comprising less than about 20% vinyl acetate by weight.

7. The endodontic fiber according to claim 6, comprising less than about 15% vinyl acetate by weight.

8. The endodontic fiber according to claim 6, comprising less than about 10% vinyl acetate by weight.

9. The endodontic fiber according to claim 6, comprising about 9.3% vinyl acetate by weight.

10. The endodontic fiber according to claim 9, having a diameter of less than about 0.5 mm and one or more medicament incorporated therein.

11. The endodontic fiber according to claim 6, having a diameter of less than about 0.5 mm.

12. The endodontic fiber of claim 6, wherein said fiber is impregnated with said one or more medicaments.

13. The endodontic fiber of claim 6, wherein said fiber has a rigidity similar to traditional gutta percha points.

14. The endodontic fiber of claim 1, wherein said fiber is impregnated with said one or more medicaments.

15. The endodontic fiber of claim 1, wherein said fiber has a rigidity similar to traditional gutta percha points.

16. A modified periodontal fiber suitable for the delivery and sustained release of one or more medicaments incorporated therein to an intracanal treatment site, comprising a polymer vehicle having incorporated therein one or more medicaments, wherein the polymer is treated to decrease its surface tackiness, wherein said endodontic fiber is capable of being positioned deep within a root canal to enable said one or more medicaments to act locally at a site of deep bacterial infection, and wherein said endodontic fiber comprises a dose of said one or more medicaments of about 2.0 mg to about 5.0 mg per 10 mm of fiber.

17. The modified periodontal fiber of claim 16, wherein said fiber is impregnated with said one or more medicaments.

18. The modified periodontal fiber of claim 6, wherein said fiber has a rigidity similar to traditional gutta percha points.

19. A method for the local delivery and sustained release of one or more medicaments to an intracanal treatment site comprising:
   (a) obtaining an endodontic fiber suitable for intracanal use having one or more medicaments incorporated therein, wherein said endodontic fiber comprises a polymer composition;
   (b) positioning the fiber of (a) in the root canal such that the fiber is in direct contact with the treatment site; and
   (c) maintaining the fiber at the treatment site, wherein the one or medicaments are delivered to the treatment site at a controlled rate;
   wherein said endodontic fiber is capable of being positioned deep within a root canal to enable said one or more medicaments to act locally at a site of deep bacterial infection, and wherein said endodontic fiber comprises a dose of said one or more medicaments of about 2.0 mg to about 5.0 mg per 10 mm of fiber.

20. The method of claim 19, wherein the endodontic fiber is a modified periodontal fiber or an intracanal fiber.

21. The method of claim 19, wherein said fiber is impregnated with said one or more medicaments.

22. The method of claim 19, wherein said fiber has a rigidity similar to traditional gutta percha points.

23. A method of treating an endodontic bacterial infection comprising the steps of:
   (a) obtaining an endodontic fiber suitable for intracanal use having one or more medicaments incorporated therein, wherein said endodontic fiber comprises a polymer composition;
   (b) positioning the fiber of (a) into a root canal such that the fiber is in direct contact with a treatment site in the root canal; and
   (c) maintaining the fiber at the treatment site, wherein the one or more medicaments are delivered to the treatment site at a controlled rate;
   wherein said endodontic fiber is capable of being positioned deep within a root canal to enable said one or more medicaments to act locally at a site of deep bacterial infection, and wherein said endodontic fiber comprises a dose of said one or more medicaments of about 2.0 mg to about 5.0 mg per 10 mm of fiber.

24. The method of claim 23, wherein the endodontic fiber is a modified periodontal fiber or an intracanal fiber.

25. The method of claim 23, wherein said fiber is impregnated with said one or more medicaments.

26. The method of claim 23, wherein said fiber has a rigidity similar to traditional gutta percha points.

27. A method of disinfecting a root canal receiving endodontic treatment comprising:
   (a) obtaining an endodontic fiber suitable for intracanal use having one or more medicaments incorporated therein, wherein said endodontic fiber comprises a polymer composition;
   (b) inserting the fiber of (a) into a debrided and irrigated root canal such that the fiber is in direct contact with a treatment site in the root canal; and
   (c) maintaining the fiber at the treatment site, wherein the one or more medicaments are administered to the treatment site at a controlled rate;
   wherein said endodontic fiber is capable of being positioned deep within a root canal to enable said one or more medicaments to act locally at a site of deep bacterial infection, and wherein said endodontic fiber comprises a dose of said one or more medicaments of about 2.0 mg to about 5.0 mg per 10 mm of fiber.

28. The method of claim 27, wherein the endodontic fiber is a modified periodontal fiber or an intracanal fiber.

29. The method of claim 27, wherein said fiber is impregnated with said one or more medicaments.

30. The method of claim 27, wherein said fiber has a rigidity similar to traditional gutta percha points.

31. A method of reducing inflammation in periapical tissue of a tooth undergoing endodontic treatment, comprising:
   (a) obtaining an endodontic fiber suitable for intracanal use having incorporated therein an anti-inflammatory agent, wherein said endodontic fiber comprises a polymer composition;
   (b) positioning the fiber of (a) into a treatment site in a debrided and irrigated root canal such that the fiber is in direct contact with an inflamed tissue in the root canal; and
   (c) maintaining the endodontic fiber at the treatment site, wherein the anti-inflammatory agent is delivered to the site of inflammation at a controlled rate;
   wherein said endodontic fiber is capable of being positioned deep within a root canal to enable said one or more medicaments to act locally at a site of deep bacterial infection, and wherein said endodontic fiber comprises a dose of said one or more medicaments of about 2.0 mg to about 5.0 mg per 10 mm of fiber.

32. The method of claim 31, wherein the endodontic fiber is a modified periodontal fiber or an intracanal fiber.

33. The method of claim 31, wherein said fiber is impregnated with said one or more medicaments.

34. The method of claim 31, wherein said fiber has a rigidity similar to traditional gutta percha points.

* * * * *

UNITED STATES PATENT AND TRADEMARK OFFICE
CERTIFICATE OF CORRECTION

| | |
|---|---|
| PATENT NO. | : 7,331,787 B2 |
| APPLICATION NO. | : 10/812638 |
| DATED | : February 19, 2008 |
| INVENTOR(S) | : Abdennour et al. |

It is certified that error appears in the above-identified patent and that said Letters Patent is hereby corrected as shown below:

On the title page, at "(73) Assignee," the Assignee name(s) should appear as follows:

Assignee: Forsyth Dental Infirmary for Children, Boston, MA (US);
President and Fellows of Harvard College, Cambridge, MA (US)

Signed and Sealed this
Nineteenth Day of July, 2011

David J. Kappos
*Director of the United States Patent and Trademark Office*